US008912125B2

(12) United States Patent
Wells

(10) Patent No.: US 8,912,125 B2
(45) Date of Patent: Dec. 16, 2014

(54) CONTROL OF TRIFLURALIN-RESISTANT WEEDS WITH DITHIOPYR

(75) Inventor: Gregory S. Wells, Sunbury (AU)

(73) Assignee: Dow AgroSciences, LLC., Indianapolis, IN (US)

( * ) Notice: Subject to any disclaimer, the term of this patent is extended or adjusted under 35 U.S.C. 154(b) by 0 days.

(21) Appl. No.: 13/253,097

(22) Filed: Oct. 5, 2011

(65) Prior Publication Data

US 2012/0088670 A1 Apr. 12, 2012

Related U.S. Application Data

(60) Provisional application No. 61/391,142, filed on Oct. 8, 2010.

(51) Int. Cl.
*A01N 43/40* (2006.01)

(52) U.S. Cl.
CPC .................................... *A01N 43/40* (2013.01)
USPC .......................................... 504/130; 504/244

(58) Field of Classification Search
None
See application file for complete search history.

(56) References Cited

U.S. PATENT DOCUMENTS

| | | | | |
|---|---|---|---|---|
| 2002/0004457 | A1 | 1/2002 | Nevill et al. | |
| 2009/0062121 | A1 | 3/2009 | Satchivi et al. | |
| 2010/0113277 | A1 | 5/2010 | Ohno et al. | |
| 2011/0009265 | A1 | 1/2011 | Sievernich et al. | |
| 2012/0021908 | A1 * | 1/2012 | Dunne et al. | 504/126 |

FOREIGN PATENT DOCUMENTS

| | | | |
|---|---|---|---|
| WO | WO 2009112486 A2 * | 9/2009 | |
| WO | WO 2012/047944 | 4/2012 | |

OTHER PUBLICATIONS

Prather et al., "Herbicide Resistance: Definition and Management Strategies", Univ. of California Division of Agriculture and Natural Resources, Publication 8012, copyright 2000, pp. 1-14.*

Wittmer et al., "Significant of urban and agricultural land use for biocide and pesticide dynamics in surface waters", Water Research, 44, (Feb. 2010), pp. 2850-2862.*

Cordain, L., "Cereal Grains: Humanity's Double-Edged Sword", World Rev Nutr Diet. Basel, Karger, 1999, vol. 84, pp. 19-73.*

Bayer CropScience, "*Lolium rigidum*," <http://www.cropscience.bayer.com/en/Crop-Compendium/Pests-Diseases-Weeds/Weeds/Lolium-rigidum.aspx> Last updated: Apr. 30, 2013, p. 1-2.*

Nufarm, "Dynamo™ 40WSP," © 2007 Nufarm Americas Inc., p. 1-8.*

CropLife Australia, "Herbicide Resistance: Mode of Action Groups," Grains Research & Development Corporation, published Nov. 2008, p. 1-6.*

Trifluralin, The Pesticide Manual, Fifteenth Edition, 2009.

Dithiopyr, The Pesticide Manual, Fifteenth Edition, 2009.

Parrish, Dithiopyr: Potential Use in European Cereals, Proc. Br. Crop. Prot. Conf. Weeds (2,573-78, 1993).

Prather, DiTomaso and Holt, History, Mechanisms, and Strategies for Prevention and Management of Herbicide Resistant Weeds, Proc. Calif. Weed Sci. Soc. (52 Meet., 155-63, 2000).

Saika, Kulshrestha, Dissipation of the Herbicide Dithiopyr in Soil and Residues in Wheat (*Triticum aestivum* L) Grain Under Indian Tropical Conditions, Pest Manag. Soc. 59(1):114-8 (Jan. 2003).

* cited by examiner

*Primary Examiner* — Tracy Vivlemore
*Assistant Examiner* — Monica Shin
(74) *Attorney, Agent, or Firm* — Michael R. Asam

(57) ABSTRACT

Methods for controlling the growth of trifluralin-resistant annual ryegrass in cereals using dithiopyr are described. The methods include contacting the locus of the cereal, at planting or before weed emergence, with an herbicidally effective amount of dithiopyr. The dithiopyr can be applied to the soil and either incorporated into the soil at the time of planting the cereal or applied post-planting to the soil surface before the weeds have emerged.

18 Claims, No Drawings

CONTROL OF TRIFLURALIN-RESISTANT WEEDS WITH DITHIOPYR

This application claims the benefit of U.S. Provisional Patent Application Ser. No. 61/391,142 filed Oct. 8, 2010.

BACKGROUND

Trifluralin, 2,6-dinitro-N,N-dipropyl-4-(trifluoromethyl) benzenamine, is a dinitroaniline (DNA) herbicide, and its herbicidal activity is described in *The Pesticide Manual*, Fifteenth Edition, 2009. Trifluralin, which acts as an inhibitor of microtubule assembly, provides pre-emergence control of many annual grass and broadleaf weeds in a variety of crops. Trifluralin has been in wide use since its introduction in the 1960s and certain weeds have developed a tolerance to both it and to other herbicides whose mode of action is that of acting as inhibitors of microtubule assembly. An effective replacement for trifluralin for the pre-emergence control of trifluralin-resistant weeds in crops would be useful.

SUMMARY

Dithiopyr, a pyridine herbicide, has surprising been found to effectively control trifluralin-resistant weeds. Methods of controlling the growth of trifluralin-resistant annual ryegrass in cereals are described. The methods include contacting the locus of the cereal, at planting or before weed emergence, with a composition containing an herbicidally effective amount of dithiopyr. The dithiopyr can be applied to the soil and either incorporated into the soil at the time of planting the cereal or applied post-planting to the soil surface before the weeds have emerged. Additional methods of controlling the growth of trifluralin-resistant annual ryegrass in cereals include applying to a field containing the cereal a composition containing a herbicidally effective amount of dithiopyr at a rate of 240 or fewer grams active ingredient per hectare

DETAILED DESCRIPTION

Dithiopyr, S,S'-dimethyl 2-(difluoromethyl)-4-(2-methylpropyl)-6-(trifluoromethyl)-3,5-pyridinedicarbothioate, is a pyridine herbicide, and its herbicidal activity is described in *The Pesticide Manual*, Fifteenth Edition, 2009. Dithiopyr is primarily used as a pre-emergent herbicide for the control of annual grass and broadleaf weeds in turf by inhibiting cell division by disrupting spindle microtubule formation.

The term herbicide is used herein to mean an active ingredient that kills, controls or otherwise adversely modifies the growth of plants. An herbicidally effective or vegetation controlling amount is an amount of active ingredient which causes an adversely modifying effect and includes deviations from natural development, killing, regulation, desiccation, retardation, and the like. The terms plants and vegetation include germinant seeds, emerging seedlings and established vegetation.

Herbicidal activity is exhibited by dithiopyr when it is applied directly to the locus of the plant before planting or emergence. The effect observed depends upon the environmental conditions at the time of use (e.g., the amount and time of rain relative to application), the specific adjuvants and carriers employed, the soil type, the planting and incorporation method (e.g., incorporated by sowing (IBS) and post-sowing pre-emergence (PSPE)) and the amount of chemical applied. Generally, the dithiopyr is applied pre-emergence or pre-plant incorporated to control the trifluralin-resistant annual ryegrass in the wheat, barley or triticale. As used herein, a composition containing an herbicidally effective amount of dithiopyr includes mixtures of dithiopyr with other components, e.g., diluted with water, as well as a composition containing only dithiopyr, i.e., a neat solution.

The dithiopyr can be applied in conjunction with one or more other cereal herbicides to control a wider variety of undesirable vegetation. When used in conjunction with other herbicides, the presently claimed compounds can be formulated with the other herbicide or herbicides, tank-mixed with the other herbicide or herbicides or applied sequentially with the other herbicide or herbicides. Some of the herbicides that can be employed in conjunction with dithiopyr include: 2,4-D, acetochlor, amidosulfuron, beflubutamid, benazolin, bentazone, bifenox, bromoxynil, butafenacil, carfentrazone-ethyl, chlortoluron, chlorsulfuron, cinidon-ethyl, clodinafop-propargyl, clopyralid, cyanazine, cyclosulfamuron, pyroxsulam, dicamba, diclofop-methyl, diflufenican, diflufenzopyr, dimefuron, dimethanamid, diuron, ethoxysulfuron, fenoxaprop, fenoxaprop-ethyl, fenoxaprop-ethyl+isoxidifen-ethyl, fenoxaprop-p-ethyl, florasulam, flucarbazone, flucetosulfuron, flumetsulam, flupyrsulfuron, flurtamone, imazamethabenz, imazamox, imazapic, imazapyr, imazaquin, imazethapyr, imazosulfuron, indanofan, iodosulfuron, iodosulfuron-ethyl-sodium, ioxynil, isoproturon, isoxaben, lactofen, linuron, MCPA, mecoprop-P, mesosulfuron, mesosulfuron-ethyl sodium, metosulam, metolachlor, metribuzin, metsulfuron, metsulfuron-methyl, orthosulfamuron, oxyfluorfen, pendimethalin, penoxsulam, picolinafen, pinoxaden, primisulfuron, profluazol, propoxycarbazone, propyzamide, prosulfocarb, prosulfuron, pyraflufen ethyl, pyroxasulfone, quinmerac, sulfosulfuron, thifensulfuron, thifensulfuron-methyl, topramezone, tralkoxydim, triallate, triasulfuron, tribenuron, tribenuron-methyl and trifluralin.

The dithiopyr can generally be employed in combination with known herbicide safeners such as cloquintocet (mexyl), benoxacor, benthiocarb, brassinolide, cyometrinil, daimuron, dichlormid, dicyclonon, dimepiperate, disulfoton, fenchlorazole-ethyl, fenclorim, flurazole, fluxofenim, furilazole, isoxadifen-ethyl, mefenpyr-diethyl, MG 191, MON 4660, naphthalic anhydride (NA), oxabetrinil, R29148 and N-phenylsulfonylbenzoic acid amides, to enhance selectivity.

While dithiopyr can be used directly as a herbicide, it is preferably used in mixtures containing a herbicidally effective amount of the compound along with at least one agriculturally acceptable adjuvant or carrier. Suitable adjuvants or carriers should not be phytotoxic to the perennial grasses, particularly at the concentrations employed in applying the compositions for grass growth regulation, and should not react chemically with the compounds or other composition ingredients. Such mixtures can be designed for application directly to grasses or their locus or can be concentrates or formulations that are normally diluted with additional carriers and adjuvants before application. They can be solids, such as, for example, dusts, granules, water-dispersible granules, or wettable powders, or liquids, such as, for example, emulsifiable concentrates, solutions, emulsions or suspensions. They can also be provided as a pre-mix or tank mixed.

Suitable agricultural adjuvants and carriers that are useful in preparing the herbicidal mixture are well known to those skilled in the art. Some of these adjuvants include, but are not limited to, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG (400) dioleate-99.

Liquid carriers that can be employed include water and organic solvents. The organic solvents typically used include, but are not limited to, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like; esters of mono, di and polycarboxylic acids and the like. Specific organic solvents include toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. Water is generally the carrier of choice for the dilution of concentrates.

Suitable solid carriers include talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, and the like.

One or more surface-active agents can be incorporated into herbicidal mixtures containing dithiopyr. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Surfactants conventionally used in the art of formulation and which may also be used in the present formulations are described, inter alia, in "McCutcheon's Detergents and Emulsifiers Annual," MC Publishing Corp., Ridgewood, N.J., 1998 and in "Encyclopedia of Surfactants," Vol. I-III, Chemical Publishing Co., New York, 1980-81. Typical surface-active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils.

Other additives commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like.

The concentration of the dithiopyr in the herbicidal mixture is generally from 0.001 to 98 percent by weight. Concentrations from 5 to 90 percent by weight are often employed. In compositions designed to be employed as concentrates, the active ingredients are generally present in a concentration from 5 to 98 weight percent, from 10 to 98 weight percent, from 20 to 98 weight percent, from 30 to 98 weight percent, from 40 to 98 weight percent, from 50 to 98 weight percent, from 60 to 98 weight percent, from 70 to 98 weight percent, from 80 to 98 weight percent, or from 90 to 98 weight percent, and preferably 5 to 90 weight percent. Such compositions are typically diluted with an inert carrier, such as water, before application. The diluted compositions usually applied to grasses or the locus of grasses generally contain 0.0001 to 1 weight percent active ingredient, 0.001 to 0.5 weight percent active ingredient, or 0.001 to 0.3 weight percent active ingredient, and preferably contain 0.001 to 0.1 weight percent.

The herbicidal mixtures as described can be applied at rates of 25 or fewer grams of active ingredient per hectare (g ai/ha), 50 or fewer g ai/ha, 75 or fewer g ai/ha, 100 or fewer g ai/ha, 110 or fewer g ai/ha, 120 or fewer g ai/ha, 130 or fewer g ai/ha, 140 or fewer g ai/ha, 150 or fewer g ai/ha, 160 or fewer g ai/ha, 170 or fewer g ai/ha, 180 or fewer g ai/ha, 190 or fewer g ai/ha, 200 or fewer g ai/ha, 210 or fewer g ai/ha, 220 or fewer g ai/ha, 230 or fewer g ai/ha, 240 or fewer g ai/ha, 250 or fewer g ai/ha, 300 or fewer g ai/ha, 350 or fewer g ai/ha, 400 or fewer g ai/ha, 450 or fewer g ai/ha, 500 or fewer g ai/ha, 600 or fewer g ai/ha, 700 or fewer g ai/ha, 800 or fewer g ai/ha, 900 or fewer g ai/ha, or 1000 or fewer g ai/ha. Preferably, the herbicidal mixtures as described can be applied at rates of 250 or fewer g ai/ha. Most preferably, the herbicidal mixtures as described can be applied at rates of 240 or fewer g ai/ha.

EXAMPLES

Five ryegrass biotypes with varying degrees of resistance to trifluralin (1251, 1216.1, 1252.6, 1252.2 and 1145.4) and two non-resistant biotypes (SLR4 and 1261.1) were tested. Dithiopyr was applied using a simulated incorporated by sowing (IBS) system for ryegrass and wheat.

Ryegrass: A set volume of seeds (50 seeds approx) were placed onto the surface of sandy potting soil in 0.55 L polyethylene pots. Dithiopyr was sprayed directly onto the ryegrass seed soil surface at rates of 250, 500 and 1000 grams active ingredient per hectare (g ai/ha). The seed and soil were then covered with a soil mixture to a depth of 5 mm (the soil mixture included 385 L peatmoss, 615 L coarse sand, 1024 g Ag. lime, 564 g hydrated lime, and 3.7 Kg Osmocote® Exact™ (Everris International B.V.; Geldermalsen, The Netherlands) with a pH of 6.3).

Wheat: Ten wheat seeds (var. *Correll*) were buried 1 cm deep. The herbicides were sprayed onto the soil surface and then the herbicide covered with another 5 mm of soil. This system of seed separation ensured crop selectivity Herbicide application was performed using a laboratory boom sprayer equipped with T-jet fan nozzles at a speed of 1 $ms^{-1}$. Output from the sprayer was calibrated at 110 L $ha^{-1}$ at a pressure of 250 kPa. Using this testing procedure, volatilization losses were minimized by the immediate and even incorporation of each herbicide. The experiment was established as a randomized block design with three replications and was conducted outdoors during mid winter (July-August).

Herbicide effects on wheat and ryegrass seedlings were measured 5 weeks after spraying. Seedlings were considered emerged if they had reached the 2-leaf stage at this time. Survival % was recorded by comparing the surviving number of 2-3 leaved seedlings in the sprayed treatments to the number present before spraying (Tables 1 and 2).

In addition, wheat biomass was recorded by harvesting the plants and measuring dry weight to indicate crop safety. The dry weights from the treated plants were compared to the weight of untreated wheat and the percentage biomass calculated (Table 2).

The present invention is not limited in scope by the embodiments disclosed herein which are intended as illustrations of a few aspects of the invention and any embodiments which are functionally equivalent are within the scope of this invention. Various modifications of the compositions and methods in addition to those shown and described herein will become apparent to those skilled in the art and are intended to fall within the scope of the appended claims. Further, while only certain representative combinations of the composition components and method steps disclosed herein are specifically discussed in the embodiments above, other combinations of the composition components and method steps will become apparent to those skilled in the art and also are intended to fall within the scope of the appended claims. Thus a combination of components or method steps may be explicitly mentioned herein; however, other combinations of components and method steps are included, even though not explicitly stated. The term "comprising" and variations thereof as used herein is used synonymously with the term "including" and variations thereof and are open, non-limiting terms.

What is claimed is:

1. A method of controlling the growth of trifluralin-resistant annual ryegrass in cereals, comprising contacting a locus of a cereal in an area that contains or will contain trifluralin-resistant annual ryegrass, at planting or before weed emergence, with a composition comprising a herbicidally effective amount of dithiopyr.

2. The method of claim 1, wherein the composition is applied to soil and either incorporated into the soil at the time of planting the cereal or applied post-planting to the soil surface before the weeds have emerged.

3. The method of claim 1, wherein the cereals are wheat, barley, or triticale.

4. The method of claim 1, wherein the composition is applied to the locus of the cereal in a composition containing 0.0001 weight percent to 1 weight percent dithiopyr.

5. The method of claim 4, wherein the composition contains 0.001 weight percent to 0.1 weight percent dithiopyr.

6. The method of claim 4, wherein the composition is created by diluting a concentrate composition containing between 0.001 percent by weight dithiopyr and 98 percent by weight dithiopyr.

7. The method of claim 1, wherein the composition is applied to a field containing the cereal at a rate of 250 or fewer grams active ingredient per hectare.

8. The method of claim 1, wherein the composition is applied to a field containing the cereal at a rate of 240 or fewer grams active ingredient per hectare.

9. A method of controlling the growth of trifluralin-resistant annual ryegrass in cereals, comprising applying to an area containing a cereal and containing or will contain the trifluralin-resistant rye grass a composition comprising dithiopyr at a rate of 250 or fewer grams active ingredient per hectare.

TABLE 1

Effect of dithiopyr applied pre-emergence on % survival of ryegrass, 5 weeks after herbicide application.

| | | Ryegrass Bio-type | | | | | | | | | | | | | |
|---|---|---|---|---|---|---|---|---|---|---|---|---|---|---|---|
| | | Bio-types without Trifluran Resistance | | | | Bio-types with Trifluran Resistance | | | | | | | | | |
| | Rate | SLR4 | | 1261.1 | | 1251 | | 1216.1 | | 1252.6 | | 1252.2 | | 1145.4 | |
| Herbicide | g ai/ha | Mean | SE | Mean | SE | Mean | SE | Mean | SE | Mean | SE | Mean | SE | Mean | SE |
| Dithiopyr | 250 | 0 | 0 | 0 | 0 | 0 | 0 | 0 | 0 | 0 | 0 | 0 | 0 | 0 | 0 |
| | 500 | 0 | 0 | 0 | 0 | 0 | 0 | 0 | 0 | 0 | 0 | 0 | 0 | 0 | 0 |
| | 1000 | 0 | 0 | 0 | 0 | 0 | 0 | 0 | 0 | 0 | 0 | 0 | 0 | 0 | 0 |
| Trifluralin | 250 | 2.9 | 2.9 | 5.6 | 5.6 | 97.7 | 9.9 | 40.4 | 3.4 | 33.8 | 17.2 | 29.1 | 8.3 | 100 | 16.5 |
| | 500 | 0 | 0 | 0 | 0 | 68.2 | 9.9 | 19.1 | 7.4 | 13.1 | 13.1 | 13.9 | 5.5 | 100 | 29.5 |
| | 1000 | 0 | 0 | 1.1 | 1.1 | 27.3 | 4.7 | 9 | 1.1 | 26.3 | 14.7 | 3.8 | 3.8 | 14.1 | 8.2 |

g ai/ha = grams of active ingredient per hectare
SE = standard error of the mean

TABLE 2

Effect of dithiopyr applied pre-emergence on % dry weight and % survival of Correll wheat, 5 weeks after herbicide application.

| Rate | Dry Weight (%) | | Survival (%) | |
|---|---|---|---|---|
| g ai/ha | Mean | SE | Mean | SE |
| 250 | 95.4 | 3.2 | 82.2 | 8.0 |
| 500 | 71.1 | 5.9 | 60.0 | 6.7 |
| 1000 | 30.6 | 9.0 | 28.9 | 4.4 |

g ai/ha = grams of active ingredient per hectare
SE = standard error of the mean 10. The method of claim 9, wherein the composition is applied to the area at planting or before weed emergence.

11. The method of claim 9, wherein the cereals are wheat, barley, or triticale.

12. The method of claim 9, wherein the composition is applied to the area at a concentration from 0.0001 weight percent to 1 weight percent dithiopyr.

13. The method of claim 12, wherein the composition contains 0.001 weight percent to 0.1 weight percent dithiopyr.

14. The method of claim 12, wherein the composition is created by diluting a concentrate composition containing between 0.001 percent by weight dithiopyr and 98 percent by weight dithiopyr.

15. The method of claim 9, wherein the composition is applied at a rate of 240 or fewer grams active ingredient per hectare.

16. The method of claim 9, wherein the composition is applied at a rate of 220 or fewer grams active ingredient per hectare.

17. The method of claim 9, wherein the composition is applied at a rate of 200 or fewer grams active ingredient per hectare.

18. A method of controlling the growth of trifluralin-resistant annual ryegrass in wheat, barley, or triticale, comprising applying to an area containing the wheat, barley, or triticale and containing or will contain the trifluralin resistant annual ryegrass, at planting or before weed emergence, a composition comprising an herbicidally effective amount of dithiopyr and one or more additional cereal herbicides, wherein the dithiopyr is applied at a rate of 250 or fewer grams active ingredient per hectare.

* * * * *